United States Patent
Galon et al.

(10) Patent No.: US 9,945,861 B2
(45) Date of Patent: Apr. 17, 2018

(54) METHODS FOR PREDICTING THE SURVIVAL TIME OF A PATIENT SUFFERING FROM A SOLID CANCER BASED ON DENSITY OF B CELLS

(71) Applicants: INSERM (INSTITUT NATIONAL DE LA SANTE ET DE LA RECHERCHE MEDICALE), Paris (FR); UNIVERSITE PARIS DESCARTES, Paris (FR); ASSISTANCE PUBLIQUE-HOPITAUX DE PARIS (APHP), Paris (FR); UNIVERSITE PIERRE ET MARIE CURIE—PARIS VI, Paris (FR)

(72) Inventors: Jerome Galon, Paris (FR); Franck Pages, Paris (FR); Bernhard Mlecnik, Paris (FR); Gabriela Bindea, Paris (FR); Herve Fridman, Paris (FR)

(73) Assignees: INSERM (INSTITUT NATIONAL DE LA SANTE ET DE LA RECHERCHE MEDICALE, Paris (FR); UNIVERSITE PARIS DESCARTES, Paris (FR); ASSISTANCE PUBLIQUE-HOPITAUX DE PARIS (APHP), Paris (FR)

(*) Notice: Subject to any disclaimer, the term of this patent is extended or adjusted under 35 U.S.C. 154(b) by 0 days.

(21) Appl. No.: 14/372,757

(22) PCT Filed: Jan. 21, 2013

(86) PCT No.: PCT/EP2013/051008
§ 371 (c)(1),
(2) Date: Jul. 17, 2014

(87) PCT Pub. No.: WO2013/107900
PCT Pub. Date: Jul. 25, 2013

(65) Prior Publication Data
US 2014/0363472 A1 Dec. 11, 2014

Related U.S. Application Data

(60) Provisional application No. 61/600,752, filed on Feb. 20, 2012.

(30) Foreign Application Priority Data

Jan. 20, 2012 (EP) .................................... 12305072

(51) Int. Cl.
G01N 33/574 (2006.01)
C12Q 1/6886 (2018.01)

(52) U.S. Cl.
CPC ..... *G01N 33/574* (2013.01); *G01N 2333/7051* (2013.01); *G01N 2333/70517* (2013.01); *G01N 2333/70589* (2013.01); *G01N 2333/70596* (2013.01); *G01N 2800/52* (2013.01)

(58) Field of Classification Search
CPC .......................... G01N 33/574; C12Q 1/6886
USPC ................................................ 435/7.23, 6.14
See application file for complete search history.

(56) References Cited

U.S. PATENT DOCUMENTS 8,481,271 B2 * 7/2013 Galon .............. G01N 33/57484
435/7.1

FOREIGN PATENT DOCUMENTS

EP 1 777 523 A1 4/2007

OTHER PUBLICATIONS

Nyi et al., "Prognostic impact of B-cell density in cutaneous melanoma", Cancer Immunology, Immunotherapy, Jul. 21, 2001, pp. 1729-1738, vol. 60, No. 12, Springer, Berlin, DE.
Mahmoud et al., "The prognostic significance of B lymphocytes in invasive carcinoma of the breast", Breast Cancer Research and Treatment, Jun. 14, 2011, pp. 545-553, vol. 132, No. 2, Kluwer Academic Publishers, BO.
Nelson, Brad H., "CD20(+) B Cells: The Other Tumor-Infiltrating Lymphocytes", Journal of Immunology, 2010, pp. 4977-4982, vol. 185, No. 9, American Association of Immunology, US.
Fridman et al., "Immune infiltration in human cancer: prognostic significance and disease control", Current Topics in Microbiology and Immunology, Jan. 1, 2011, pp. 1-24, vol. 344, Springer, Berlin, DE.

* cited by examiner

*Primary Examiner* — Yan Xiao
(74) *Attorney, Agent, or Firm* — Whitham, Curtis & Cook, P.C.

(57) ABSTRACT

The present invention relates to a method for predicting the survival time of a patient suffering from a solid cancer comprising the steps consisting of i) determining the density of B cells at the invasive margin of the tumor (im) in a tumor tissue sample obtained from said patient, ii) comparing said density with a predetermined reference value and iii) providing a good prognosis when the density of B cells at the invasive margin of the tumor is higher than the predetermined reference value and a poor prognosis when the density of B cells at the invasive margin of the tumor is lower than the predetermined reference value.

7 Claims, 6 Drawing Sheets

Figure 1:
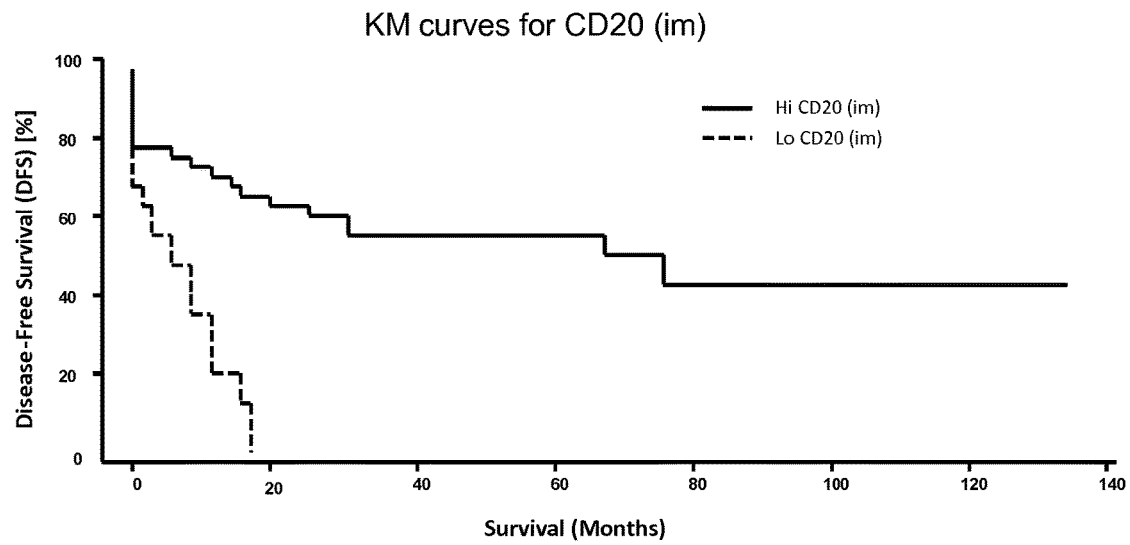

METHODS FOR PREDICTING THE SURVIVAL TIME OF A PATIENT SUFFERING FROM A SOLID CANCER BASED ON DENSITY OF B CELLS

FIELD OF THE INVENTION

The present invention relates to methods and kits for the prognosis of survival time of a patient suffering from a solid cancer.

BACKGROUND OF THE INVENTION

Cancer is a complex disease involving interactions between the immune system and the tumour[1]. The correlation between a "high" intra- and peri-tumoural adaptive immune reaction in colorectal carcinoma and a good prognosis was previously reported. In contrast, a "low" density of T cells was correlated with a poor prognosis[2-4]. In fact, of all the various clinical and histopathologic criteria currently available[5,6], the immune T cell infiltrate was shown to be the most important predictive criteria for survival[2,7-9]. This is also supported by mouse models of immunosurveillance and immunoediting[10-12]. Recent advances in cellular immunology and tumour biology are guiding new approaches to adoptive T-cell therapy[13] with promising results[14]. However there is still a need for other reliable methods that will help physicians for predicting the outcome of a cancer in a patient.

SUMMARY OF THE INVENTION

The present invention relates to a method for predicting the survival time of a patient suffering from a solid cancer comprising the steps consisting of i) determining the density of B cells at the invasive margin of the tumor (im) in a tumor tissue sample obtained from said patient, ii) comparing said density with a predetermined reference value and iii) providing a good prognosis when the density of B cells at the invasive margin of the tumor is higher than the predetermined reference value and a poor prognosis when the density of B cells at the invasive margin of the tumor is lower than the predetermined reference value.

DETAILED DESCRIPTION OF THE INVENTION

Applying integrative analyses, the inventors investigated gene expression and cell densities from 28 different cell types comprising most innate and adaptive immune-cell subpopulations in tumours. They found clusters of immune-cells associated with a specific tumour stage. Among them, B and T lymphocytes are organized within a core network and are the most prominent immune cells correlating with tumour progression and a favourable prognosis. More particularly, the inventors demonstrated that patients with high density of B cells in the invasive margin of the tumor had a prolonged disease-free survival whereas patients with low density of B cells in the invasive margin of the tumor had a poor prognosis. The combination of B cell marker with at least one marker selected from the group consisting of CD3, CD8 and CDR45RO in at least one region of the tumor (im and/or ct) gave also a better discrimination of patients.

Accordingly, the present invention relates to a method for predicting the survival time of a patient suffering from a solid cancer comprising the steps consisting of i) determining the density of B cells at the invasive margin of the tumor (im) in a tumor tissue sample obtained from said patient ii) comparing said density with a predetermined reference value and iii) providing a good prognosis when the density of B cells at the invasive margin of the tumor is higher than the predetermined reference value and a poor prognosis when the density of B cells at the invasive margin of the tumor is lower than the predetermined reference value.

In one embodiment the patient suffers from a cancer selected from the group consisting of adrenal cortical cancer, anal cancer, bile duct cancer (e.g. periphilar cancer, distal bile duct cancer, intrahepatic bile duct cancer), bladder cancer, bone cancer (e.g. osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancer (e.g. meningioma, astocytoma, oligodendrogliomas, ependymoma, gliomas, medulloblastoma, ganglioglioma, Schwannoma, germinoma, craniopharyngioma), breast cancer (e.g. ductal carcinoma in situ, infiltrating ductal carcinoma, infiltrating lobular carcinoma, lobular carcinoma in situ, gynecomastia), Castleman disease (e.g. giant lymph node hyperplasia, angiofollicular lymph node hyperplasia), cervical cancer, colorectal cancer, endometrial cancer (e.g. endometrial adenocarcinoma, adenocanthoma, papillary serous adnocarcinoma, clear cell), esophagus cancer, gallbladder cancer (mucinous adenocarcinoma, small cell carcinoma), gastrointestinal carcinoid tumors (e.g. choriocarcinoma, chorioadenoma destruens), Hodgkin's disease, non-Hodgkin's lymphoma, Kaposi's sarcoma, kidney cancer (e.g. renal cell cancer), laryngeal and hypopharyngeal cancer, liver cancer (e.g. hemangioma, hepatic adenoma, focal nodular hyperplasia, hepatocellular carcinoma), lung cancer (e.g. small cell lung cancer, non-small cell lung cancer), mesothelioma, plasmacytoma, nasal cavity and paranasal sinus cancer (e.g. esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g. embryonal rhabdomyosarcoma, alveolar rhabdomyosarcoma, pleomorphic rhabdomyosarcoma), salivary gland cancer, skin cancer (e.g. melanoma, nonmelanoma skin caner), stomach cancer, testicular cancer (e.g. seminoma, nonseminoma germ cell cancer), thymus cancer, thyroid cancer (e.g. follicular carcinoma, anaplastic carcinoma, poorly differentiated carcinoma, medullary thyroid carcinoma, thyroid lymphoma), vaginal cancer, vulvar cancer, and uterine cancer (e.g. uterine leiomyosarcoma).

As used herein, the term "tumor tissue sample" has its general meaning in the art and encompasses pieces or slices of tissue that have been removed including following a surgical tumor resection or following the collection of a tissue sample for biopsy. The tissue tumor sample shall comprise the invasive margin surrounding the tumor, and may comprise or not the center of the tumor. As used herein the "invasive margin" has its general meaning in the art and refers to the cellular environment surrounding the tumor. The tumor tissue sample can, of course, be subjected to a variety of well-known post-collection preparative and storage techniques (e.g., fixation, storage, freezing, etc.) prior to determining the density of B cells at the invasive margin of the tumor (im). Typically the tissue tumor sample may be paraffin-embedded or frozen.

The method of the invention is particularly suitable for the duration of the disease-free survival (DFS) or the overall survival (OS).

As used herein, the term "B cell" has its general meaning in the art and refers to a cell produced in the bone marrow expressing membrane-bound antibody specific for an antigen. Following interaction with the antigen it differentiates into a plasma cell which secretes antibodies specific for the antigen or into a memory B cell. "B cell" and "B lymphocyte" is used interchangeably. Typically, B cells are characterized by expression of B cell markers at their cell surface. As used herein, the term "B cell marker" refers to surface molecules on the B cells which are specific for particular B cells. B cell markers suitable for use in the present invention include, but are not limited to surface IgG, kappa and lambda chains, Ig-alpha (CD79alpha), Ig-beta (CD79beta), CD19, B220 (CD45R), CD20, CD21, CD22, CD23, CD27, or any other CD antigen specific for B cells. Typically a B cell is a CD20+ cell.

Determining the density of B cells at the invasive margin of the tumor may be determined by any well known method in the art. Typically, such methods comprise contacting the tumor tissue sample with at least one selective binding agent capable of selectively interacting with B cells. The selective binding agent may be polyclonal antibody or monoclonal antibody, an antibody fragment, synthetic antibodies, or other protein-specific agents such as nucleic acid or peptide aptamers. Typically, the selective binding agent binds any of the B cell markers, such as an antibody specific for any of these molecules. Preferred B cell selective binding agents bind to CD19, CD20, CD21, CD22 or CD37. Particularly preferred B cell selective binding agents bind to CD20. Several antibodies have been described in the prior art and many antibodies are also commercially available such as described in the EXAMPLE. For the detection of the antibody that makes the presence of the B cells detectable by microscopy or an automated analysis system, the antibodies may be tagged directly with detectable labels such as enzymes, chromogens or fluorescent probes or indirectly detected with a secondary antibody conjugated with detectable labels.

The preferred method according to the present invention is immunohistochemistry. Typically, the tissue tumor sample is firstly incubated with labeled antibodies directed against one B cell marker of interest (e.g. CD20). After washing, the labeled antibodies that are bound to said B cell marker of interest are revealed by the appropriate technique, depending of the kind of label is borne by the labeled antibody, e.g. radioactive, fluorescent or enzyme label. Multiple labelling can be performed simultaneously. Alternatively, the method of the present invention may use a secondary antibody coupled to an amplification system (to intensify staining signal) and enzymatic molecules. Such coupled secondary antibodies are commercially available, e.g. from Dako, EnVision system. Counterstaining may be used, e.g. H&E, DAPI, Hoechst. Other staining methods may be accomplished using any suitable method or system as would be apparent to one of skill in the art, including automated, semi-automated or manual systems.

As used herein, the density of B cells may be expressed as the number of these cells that are counted per one unit of surface area of tissue sample, e.g. as the number of B cells that are counted per $cm^2$ or $mm^2$ of surface area of tumor tissue sample. As used herein, the density of B cells may also be expressed as the number of B cells per one volume unit of sample, e.g. as the number of B cells per $cm3$ of tumor tissue sample. As used herein, the density of B cells may also consist of the percentage of B cells per total cells (set at 100%).

Predetermined reference values used for comparison may consist of "cut-of" values that may be determined as described hereunder. Each reference ("cut-off") value for each biological marker may be predetermined by carrying out a method comprising the steps of a) providing a collection of tumor tissue samples from cancer patients;

b) providing, for each tumor tissue sample provided at step a), information relating to the actual clinical outcome for the corresponding cancer patient (i.e. the duration of the disease-free survival (DFS) or the overall survival (OS));

c) providing a serial of arbitrary quantification values;

d) determining the B cells density at the invasive margin of the tumor for each tumor tissue sample contained in the collection provided at step a);

e) classifying said tumor tissue samples in two groups for one specific arbitrary quantification value provided at step c), respectively: (i) a first group comprising tissue tumor samples that exhibit a quantification value for said density that is lower than the said arbitrary quantification value contained in the said serial of quantification values; (ii) a second group comprising tumor tissue samples that exhibit a quantification value said density that is higher than the said arbitrary quantification value contained in the said serial of quantification values; whereby two groups of tumor tissue samples are obtained for the said specific quantification value, wherein the tumors tissue samples of each group are separately enumerated;

f) calculating the statistical significance between (i) the quantification value obtained at step e) and (ii) the actual clinical outcome of the patients from which tumor tissue samples contained in the first and second groups defined at step f) derive;

g) reiterating steps f) and g) until every arbitrary quantification value provided at step d) is tested;

h) setting the said predetermined reference value ("cut-off" value) as consisting of the arbitrary quantification value for which the highest statistical significance (most significant) has been calculated at step g).

As it is disclosed above, said method allows the setting of a single "cut-off" value permitting discrimination between poor and good prognosis. Practically, as it is disclosed in the examples herein, high statistical significance values (e.g. low P values) are generally obtained for a range of successive arbitrary quantification values, and not only for a single arbitrary quantification value. Thus, in one alternative embodiment of the method of determining "cut-off" values above, a minimal statistical significance value (minimal threshold of significance, e.g. maximal threshold P value) is arbitrarily set and the range of arbitrary quantification values for which the statistical significance value calculated at step g) is higher (more significant, e;g. lower P value) are retained, whereby a range of quantification values is provided. Said range of quantification values consist of a "cut-off" value according to the invention. According to this specific embodiment of a "cut-off" value, poor or good clinical outcome prognosis can be determined by comparing the B cell density determined at step i) with the range of values delimiting the said "cut-off" value. In certain embodiments, a cut-off value consisting of a range of quantification values, consists of a range of values centered on the quantification value for which the highest statistical significance value is found (e;g. generally the minimum P value which is found).

Typically, the predetermined reference value may consist of the B cell density value (e.g. density of CD20+ cells), per total cells (set at 100%), that correlates with a poor prognosis (e.g. a short disease-free survival time), or in contrast may consist of the B cell density value that correlates with good prognosis (e.g. a long disease-free survival time).

In a particular embodiment the comparison steps may include a classification of the quantification values measured for the cell density in two groups, respectively: (i) a first group termed "Hi" when the quantification value for the cell density is higher than the predetermined corresponding reference value and (ii) a second group termed "Lo" when the quantification value for the cell density is lower than the predetermined corresponding reference value. It flows from the example that if the result of the comparison step consists of a "Hi" value, then a good prognosis is provided (FIG. 1). Conversely, if the result of the comparison step consists of a "Lo" value, then a poor prognosis is provided (FIG. 1). A score may be also determined according to table 1.

The method of the invention may further comprises the steps consisting of i) determining the density of at least one further cell type at the invasive margin of the tumor (im) and/or at the center of the tumor (ct) in a tumor tissue sample obtained from said patient and ii) comparing said density with a predetermined reference value.

Typically the further cell type is selected from the group consisting of T cells or among a particular subset of T cells including cytotoxic T cells or memory T cells.

As used herein, the term "T cell" has its general meaning in the art and includes cells within the T cell lineage, including thymocytes, immature T cells, mature T cells and the like. Typically, T cells are characterized by expression of T cell markers at their cell surface. As used herein, the term "T cell marker" refers to surface molecules on the T cells which are specific for particular T cells. T cell markers suitable for use in the present invention include, but are not limited to surface CD3, CD4, CD8, CD45RO or any other CD antigen specific for T cells. Typically a T cell is a CD3+ cell.

As used herein the term "cytotoxic T cells" has its general meaning in the art and refers to a T cell, once activated by a MHC-antigen complex, releases the protein perforin, which forms pores in the target cell's plasma membrane; this causes ions and water to flow into the target cell, making it expand and eventually lyse. Cytotoxic T cells also release granzyme, a serine protease that can enter target cells via the perforin-formed pore and induce apoptosis (cell death). Most cytotoxic T cells have present on the cell surface the protein CD8, which is attracted to portions of the Class I MHC molecule. Typically a cytotoxic T cell is a CD8+ cell.

As used herein the term "memory T cell" has its general meaning in the art and to a subset of T cells that are specific to the antigen they first encountered and can be called upon during the secondary immune response. Memory T cells are characterized by the expression at their cell surface of CDR45RO. Typically a memory T cell is a CD45RO+ cell.

In a particular embodiment the method of the invention may further comprise the steps consisting of i) determining the density of T cells in the center of the tumor (ct) in a tumor tissue sample obtained from said patient and ii) comparing said density with a predetermined reference value.

In a particular embodiment the method of the invention may further comprise the steps consisting of i) determining the density of T cells at the invasive margin (im) of the tumor in a tumor tissue sample obtained from said patient and ii) comparing said density with a predetermined reference value.

In a particular embodiment the method of the invention may further comprise the steps consisting of i) determining the density of T cells in the center of the tumor (ct) in a tumor tissue sample obtained from said patient ii) determining the density of T cells at the invasive margin (im) of the tumor in a tumor tissue sample obtained from said patient and iii) comparing said densities with predetermined reference values.

In a particular embodiment the method of the invention may further comprise the steps consisting of determining the density of cytotoxic T cells in the center of the tumor (ct) in a tumor tissue sample obtained from said patient and ii) comparing said density with a predetermined reference value.

In a particular embodiment the method of the invention may further comprise the steps consisting of determining the density of cytotoxic T cells at the invasive margin (im) of the tumor in a tumor tissue sample obtained from said patient and ii) comparing said density with a predetermined reference value.

In a particular embodiment the method of the invention may further comprise the steps consisting of i) determining the density of cytotoxic T cells in the center of the tumor (ct) in a tumor tissue sample obtained from said patient ii) determining the density of cytotoxic T cells at the invasive margin (im) of the tumor in a tumor tissue sample obtained from said patient and iii) comparing said densities with predetermined reference values.

In a particular embodiment the method of the invention may further comprise the steps consisting of determining the density of cytotoxic T cells in the center of the tumor (ct) in a tumor tissue sample obtained from said patient and ii) comparing said density with a predetermined reference value.

In a particular embodiment the method of the invention may further comprise the steps consisting of determining the density of memory T cells in the center of the tumor (ct) in a tumor tissue sample obtained from said patient and ii) comparing said density with a predetermined reference value.

In a particular embodiment the method of the invention may further comprise the steps consisting of determining the density of memory T cells at the invasive margin (im) of the tumor in a tumor tissue sample obtained from said patient and ii) comparing said density with a predetermined reference value.

In a particular embodiment the method of the invention may further comprise the steps consisting of i) determining the density of memory T cells in the center of the tumor (ct) in a tumor tissue sample obtained from said patient ii) determining the density of memory T cells at the invasive margin (im) of the tumor in a tumor tissue sample obtained from said patient and iii) comparing said densities with predetermined reference values.

For said additional cell densities the comparison steps may also include a classification of the quantification values measured for each cell density in two groups, respectively: (i) a first group termed "Hi" when the quantification value for cell density is higher than the predetermined corresponding reference value and (ii) a second group termed "Lo" when the quantification value for the cell density is lower than the predetermined corresponding reference value.

A score which is a composite of classification done for the B cell density and for the additional densities may also be calculated as depicted in tables 1-9 to make easier to understand the result of the comparison step.

The methods of the invention are of higher accuracy than currently used staging methods (e.g. UICC-TNM). Accordingly, the methods of the invention can be applied for monitoring the effectiveness of anti-cancer treatments. For example, the present invention provides a method for monitoring the effectiveness of treatment of a subject with an agent comprising the steps of (i) predicting the survival time of the patient before administering said agent by performing the method according to the invention, ii) predicting the survival time of the patient after administering said agent by performing the method according to the invention iii) comparing the survival time of step a) with the survival time of step b) and iv) and providing the conclusion that the agent is effective for the treatment of the cancer when the survival time of step b) is higher than the survival time of step a). In case where the conclusion is negative then the physician may adapt the treatment by prescribing different dosage or by prescribing another agent to administer. The methods of the invention may also particularly suitable for determining whether the patient will be considered as responder to the treatment (e.g. an immunotherapy agent). Typically, when a good prognosis is provided by the methods of the invention the patient may be eligible for the treatment. The methods of the invention may also particularly suitable for determining whether adjuvant therapy (e.g. chemotherapy) will be required or not. For example, when a good prognosis is provided by the method of the invention, the subsequent anti-cancer treatment may not comprise any adjuvant chemotherapy. However when a poor prognosis is provided by the method of the invention, then the patient my eligible for the adjuvant chemotherapy.

The present invention includes a kit for performing the method of the present invention comprising means for determining the cell density as above described. For example, a kit according to the invention may comprise comprises one or a combination or a set of antibodies, each kind of antibodies being directed specifically against one cell type. Suitable means include antibodies, antibody derivatives, antibody fragments, and the like. The kit of the invention may optionally comprise additional components useful for performing the methods of the invention. By way of example, the kit may comprise fluids (e.g. buffers), one or more sample compartments, an instructional material which describes performance of the method of the invention, and the like.

The invention will be further illustrated by the following figures and examples. However, these examples and figures should not be interpreted in any way as limiting the scope of the present invention.

FIGURES

FIG. 1: Kaplan Meier curves illustrate the duration of Disease free survival according to the CD20 cells density in the invasive margin (im) of the tumor (test cohort, n=107). The cutoff value for the density of cells was defined at the optimal p-value of the cohort.

Figure 2:
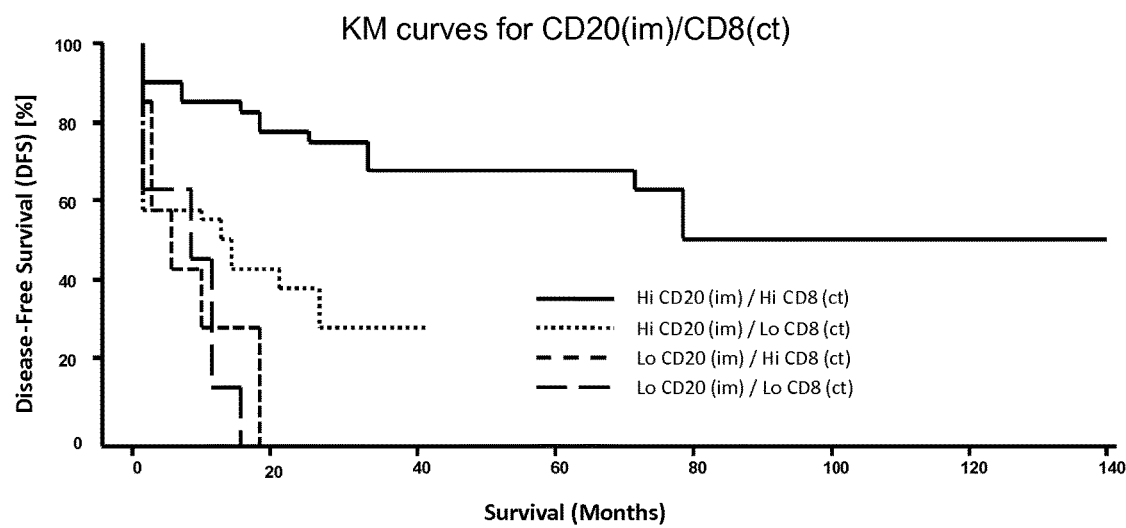

FIG. 2: Kaplan Meier curves illustrate the duration of Disease free survival according to the CD20 cells density in the invasive margin (im) of the tumor in combination with CD8 cells density in the center (ct) of the tumor (test cohort, n=107). The cutoff value for the density of CD20 and CD8 cells was defined at the optimal p-value of the cohort.

Figure 3:
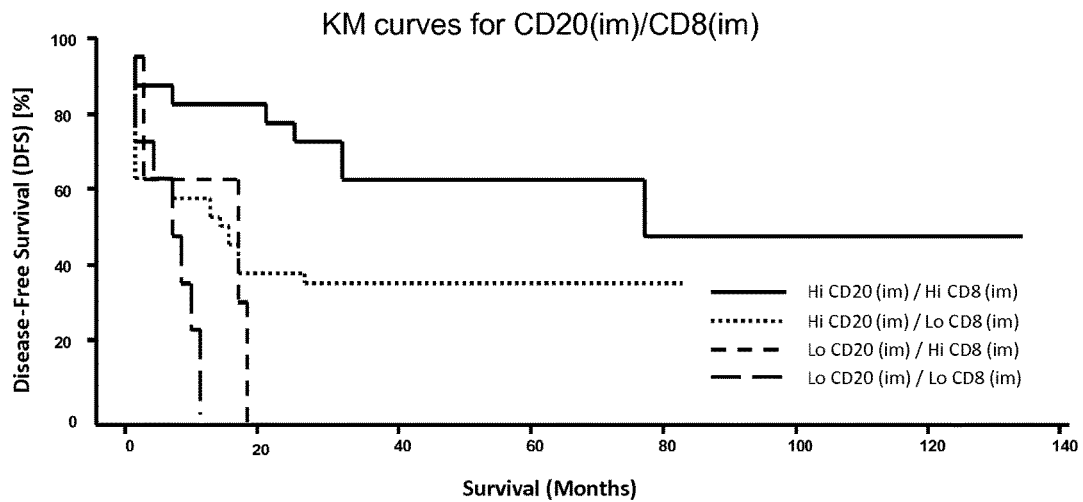

FIG. 3: Kaplan Meier curves illustrate the duration of Disease free survival according to the CD20 cells density in the invasive margin (im) of the tumor in combination with CD8 cells density in invasive margin (im) of the tumor (test cohort, n=107). The cutoff value for the density of CD20 and CD8 cells was defined at the optimal p-value of the cohort.

Figure 4:
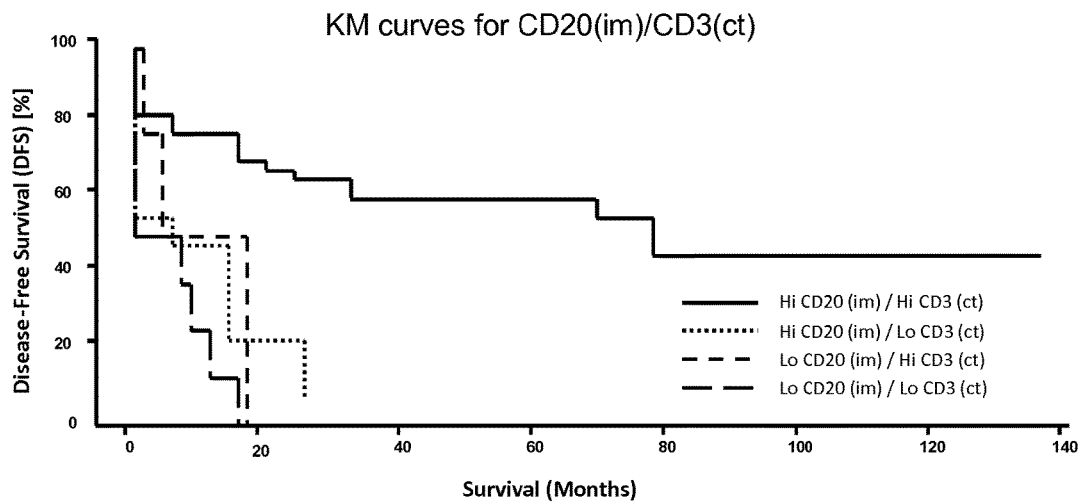

FIG. 4: Kaplan Meier curves illustrate the duration of Disease free survival according to the CD20 cells density in the invasive margin (im) of the tumor in combination with CD3 cells density in the center (ct) of the tumor (test cohort, n=107). The cutoff value for the density of CD20 and CD3 cells was defined at the optimal p-value of the cohort.

Figure 5:
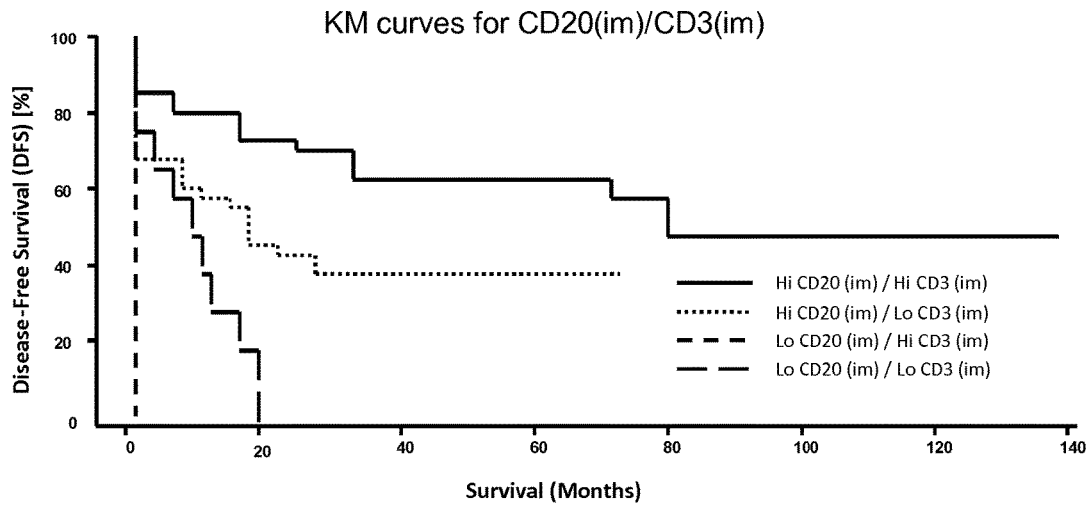

FIG. 5: Kaplan Meier curves illustrate the duration of Disease free survival according to the CD20 cells density in the invasive margin (im) of the tumor in combination with CD3 cells density in invasive margin (im) of the tumor (test cohort, n=107). The cutoff value for the density of CD20 and CD3 cells was defined at the optimal p-value of the cohort.

Figure 6:
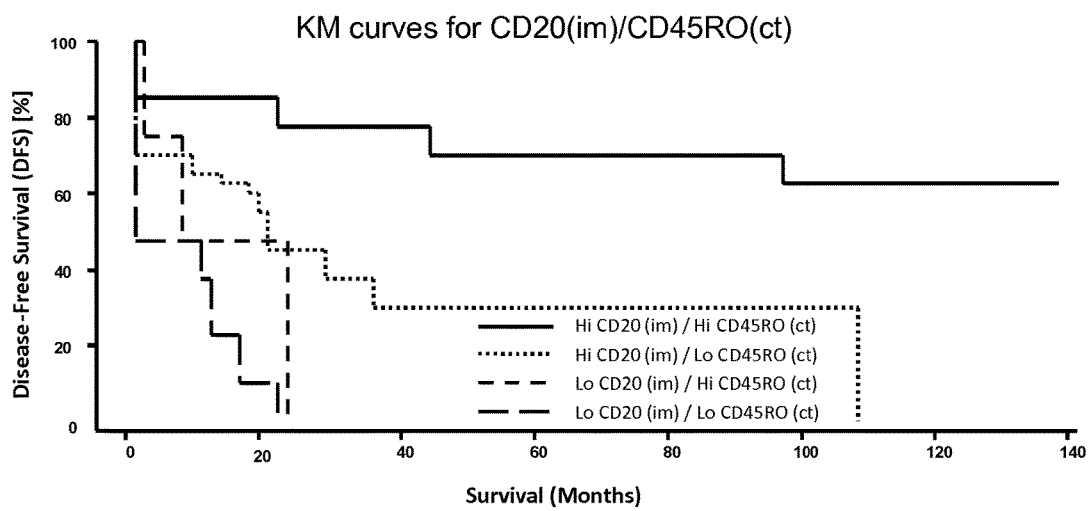

FIG. 6: Kaplan Meier curves illustrate the duration of Disease free survival according to the CD20 cells density in the invasive margin (im) of the tumor in combination with CD45RO cells density in the center (ct) of the tumor (test cohort, n=107). The cutoff value for the density of CD20 and CD45RO cells was defined at the optimal p-value of the cohort.

Figure 7:
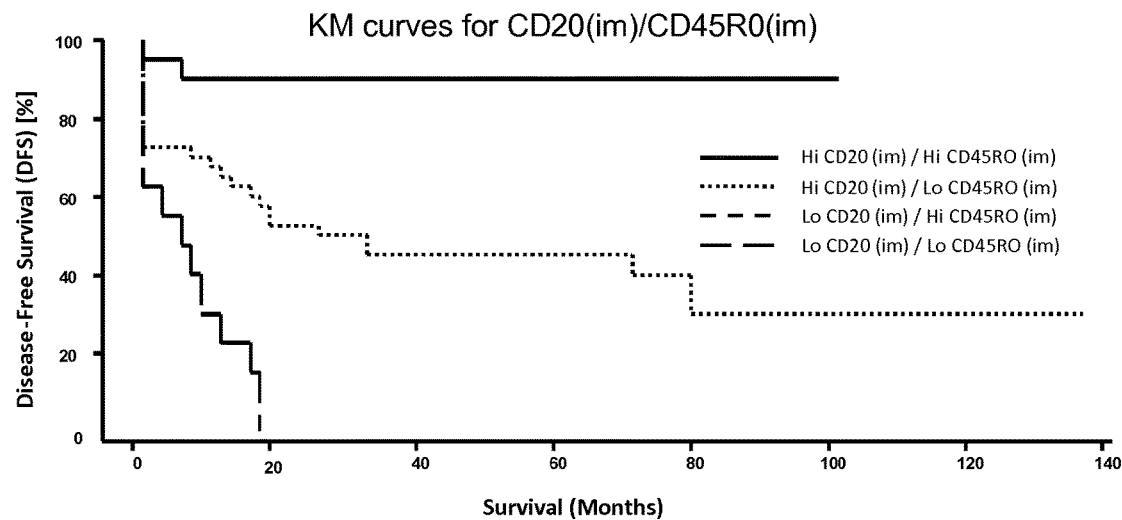

FIG. 7: Kaplan Meier curves illustrate the duration of Disease free survival according to the CD20 cells density in the invasive margin (im) of the tumor in combination with CD45RO cells density in invasive margin (im) of the tumor (test cohort, n=107). The cutoff value for the density of CD20 and CD45RO cells was defined at the optimal p-value of the cohort.

Figure 8:
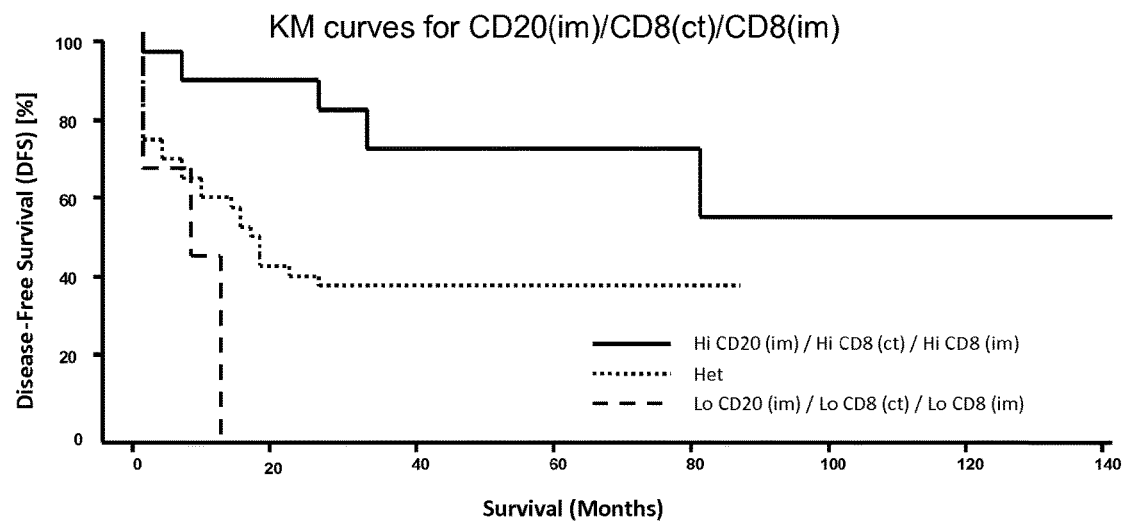

FIG. 8: Kaplan Meier curves illustrate the duration of Disease free survival according to the CD20 cells density in the invasive margin (im) of the tumor in combination with CD8 cells density in the center (ct) and in the invasive margin (im) of the tumor (test cohort, n=107). The cutoff value for the density of CD20 and CD8 cells was defined at the optimal p-value of the cohort. The group "het" illustrate the duration of Disease free survival of combinations of Hi or Lo CD20 cells density in the invasive margin (im) with Hi or Lo CD8 cells in the centre (ct) and in the invasive margin of the tumor (im).

Figure 9:
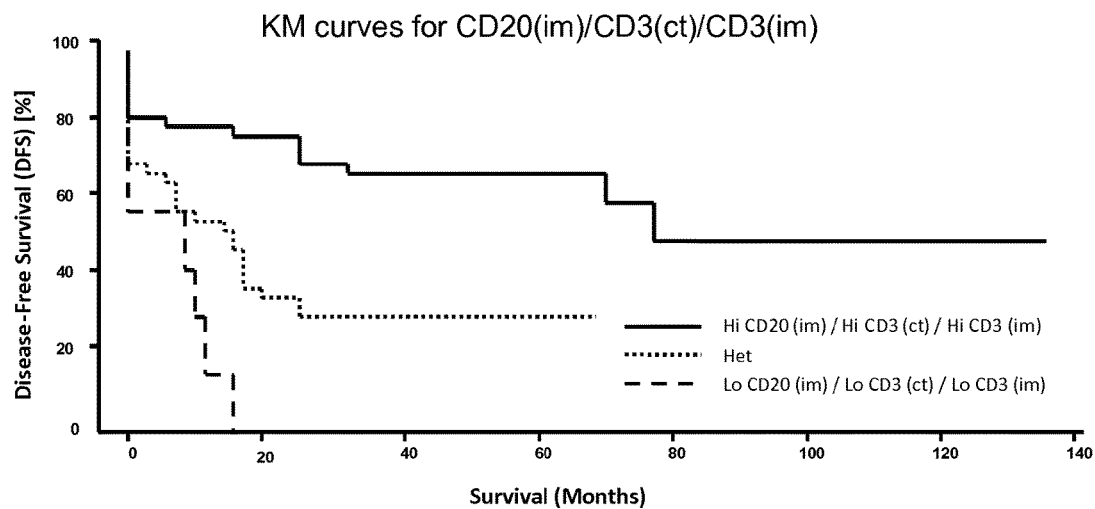

FIG. 9: Kaplan Meier curves illustrate the duration of Disease free survival according to the CD20 cells density in the invasive margin (im) of the tumor in combination with CD3 cells density in the center (ct) and in the invasive margin (im) of the tumor (test cohort, n=107). The cutoff value for the density of CD20 and CD3 cells was defined at the optimal p-value of the cohort. The group "het" illustrate the duration of Disease free survival of combinations of Hi or Lo CD20 cells density in the invasive margin (im) with Hi or Lo CD3 cells in the centre (ct) and in the invasive margin of the tumor (im).

Figure 10:
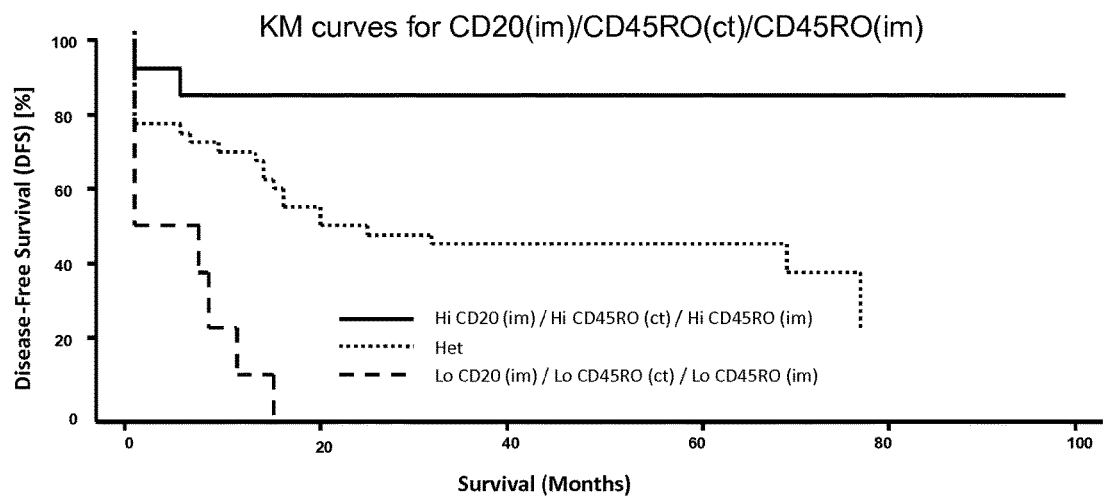

FIG. 10: Kaplan Meier curves illustrate the duration of Disease free survival according to the CD20 cells density in the invasive margin (im) of the tumor in combination with CD45RO cells density in the center (ct) and in the invasive margin (im) of the tumor (test cohort, n=107). The cutoff value for the density of CD20 and CD45RO cells was defined at the optimal p-value of the cohort. The group "het" illustrate the duration of Disease free survival of combinations of Hi or Lo CD20 cells density in the invasive margin (im) with Hi or Lo CD45RO cells in the centre (ct) and in the invasive margin of the tumor (im).

Figure 11:
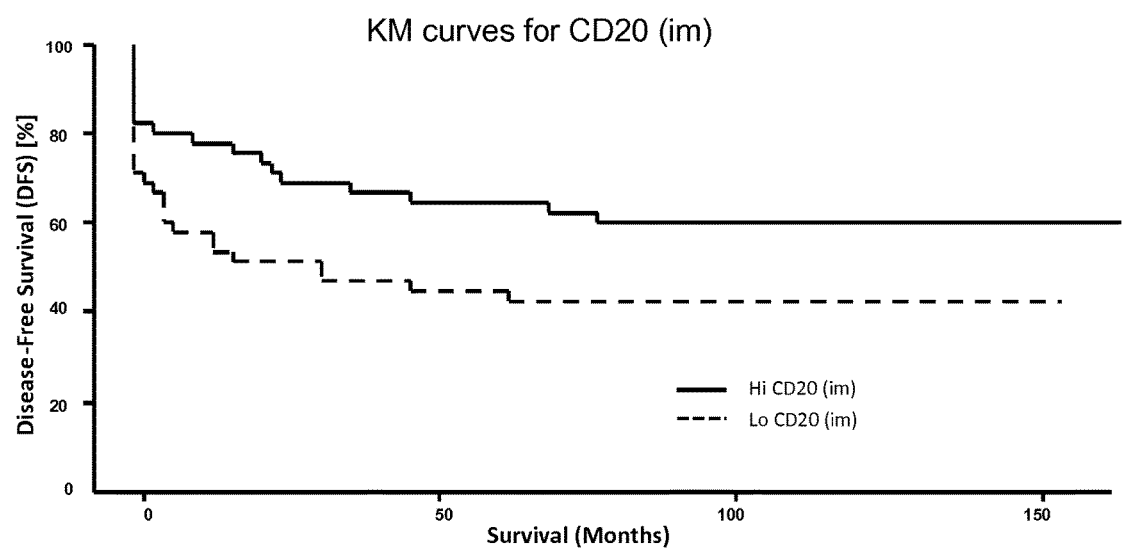

FIG. 11: Kaplan Meier curves illustrate the duration of Disease free survival according to the CD20 cells density in the invasive margin (im) of the tumor (validation cohort, n=415). The cutoff value for the density of cells was defined at the optimal p-value of the cohort.

EXAMPLE 1

Material & Methods:
Patients:
Patients with colorectal cancer who underwent a primary resection at the Laennec/HEGP (Hopital Europpeen George Pompidou) Hospital were randomly selected (n=107). The validation cohort (n=415) was previously described (Galon J, Costes A, Sanchez-Cabo F, et al. Type, density, and location of immune cells within human colorectal tumors predict clinical outcome. Science 2006; 313:1960-4.). Time to recurrence or disease-free time was defined as the time period from the date of surgery to the confirmed tumor relapse date for relapsed patients and from the date of surgery to the date of last follow-up for disease-free patients. A secure Web-based database, TME.db, integrated the clinical data and the data from high-throughput technologies (36).

Tissue Microarrays Construction
Using a tissue microarray instrument (Beecher Instruments, Alphelys, Plaisir, France), we selected two different and representative areas of the tumor. The center of the tumor (ct) and the invasive margin (im) were punched (0.6 mm and 1 mm-diameter, respectively) from paraffin-embedded tissue-blocks. Tissue microarrays were constructed and cut into 5-μm sections for immunohistochemical staining Immunohistochemistry
After antigen retrieval and quenching of endogenous peroxidase activity, sections were incubated for 60 min at room temperature with antibodies against CD3 (SP7), CD8 (4B11), CD45RO (OPD4) and CD20 (L26; DAKO, Carpinteria, Calif.). Envision+ system (enzyme-conjugated polymer backbone coupled to secondary antibodies) and DAB-chromogen were applied (Dako, Copenhagen, Denmark). Tissue sections were counterstained with Harris's hematoxylin. Slides were analyzed using an image analysis workstation (SpotBrowser, Alphelys, Plaisir, France). The density was recorded as the number of positive cells per tissue surface area ($mm^2$). For each duplicate, the mean density was used for further statistical analysis.

Statistical Analysis
Kaplan-Meier curves were used to assess the influence of immune parameters on disease-free survival. The significance of these parameters was calculated with the log-rank test. We applied cutoffs based on the patients' disease-free survival using the median and "minimum P-value" approach to separate patients into a Hi and Lo group. For pairwise comparisons Wilcoxon rank-sum test was used. $P<0.05$ was considered statistically significant. All analyzes were performed with the statistical software R and Statview.

Results:
In situ studies using tissue microarray from the center and the invasive margin of the tumor were performed. Immunostaining for B cells (CD20), T cells (CD3), cytotoxic T cells (CD8) and memory T cells (CD45RO) were quantified with a dedicated image analysis workstation. A precise measurement of intratumoral immune cell density was performed by counting the immune cells and measuring the surface area of the tissue. We evaluated the disease-free survival according to the B cell density. Kaplan-Meier curves illustrated the pejorative effect of CD20 on patient's survival (FIGS. 1-10) in combination or no with cells (CD3) and cytotoxic T cells (CD8) and memory T cells (CD45RO) densities. Patients with high CD20 density in the invasive margin of the tumors had a better disease-free survival than patients with low CD20 density in the centre region (FIG. 1). The combination of the CD20 and CD3, CD8 and CDR45RO markers defined groups of patients with very different outcome. For example patients with CD20 Lo (im) and at least one "Lo" marker selected from the group consisting of CD3, CD8 and CDR45RO in at least one region of the tumors had a dramatic outcome. In contrast, patients with CD20 Hi (im) and at least one "Hi" marker selected from the group consisting of CD3, CD8 and CDR45RO in at least one region of the tumors had a good outcome (Table 11). We validated the results by analyzing an independent cohort of 415 colorectal cancer patients by tissue microarrays. Similar results were found (FIG. 11). Longer disease-free survival was observed among patients with tumor containing a high density of CD20+ cells in the invasive margin of the tumors (Hi CD20 (im)), and patients with at least one "Hi" marker selected from the group consisting of CD3, CD8 and CDR45RO in at least one region of the tumors (im and/or ct) had the best outcome. Similar hazard-ratios and P-values were found in both cohorts.

Conclusion:
In conclusion patients with high density of B cells in the invasive margin of the tumor had a prolonged disease-free survival whereas patients with low density of B cells in the invasive margin of the tumor had a poor prognosis. The combination of this marker with at least one marker selected from the group consisting of CD3, CD8 and CDR45RO in at least one region of the tumor (im and/or ct) gave also a better discrimination of patients. Immunological scores may be then calculated according to tables 1-10.

TABLE 1 scores for CD20 (im)

| Name | Combination | Prognosis | Score |
|---|---|---|---|
| Hi | Hi CD20 (im) | Good | 1 |
| Lo | Lo CD20 (im) | Poor | 0 |

TABLE 2 scores for combinations of CD20 (im) and CD8 (ct):

| Name | Combination | Prognosis | Score |
|---|---|---|---|
| HiHi | Hi CD20 (im)/Hi CD8 (ct) | Good | 2 |
| Het | [Hi CD20 (im)/Lo CD8 (ct)] or [Lo CD20 (im)/Hi CD8 (ct)] | intermediate | 1 |
| LoLo | Lo CD20 (im)/Lo CD8 (ct) | Poor | 0 |

TABLE 3 scores for combinations of CD20 (im) and CD8 (im):

| Name | Combination | Prognosis | Score |
|---|---|---|---|
| HiHi | Hi CD20 (im)/Hi CD8 (im) | Good | 2 |
| Het | [Hi CD20 (im)/Lo CD8 (im)] or [Lo CD20 (im)/Hi CD8 (im)] | intermediate | 1 |
| LoLo | Lo CD20 (im)/Lo CD8 (im) | Poor | 0 |

TABLE 4 scores for combinations of CD20 (im) and CD3 (ct):

| Name | Combination | Prognosis | Score |
|---|---|---|---|
| HiHi | Hi CD20 (im)/Hi CD3 (ct) | Good | 2 |
| Het | [Hi CD20 (im)/Lo CD3 (ct)] or [Lo CD20 (im)/Hi CD3 (ct)] | intermediate | 1 |
| LoLo | Lo CD20 (im)/Lo CD3 (ct) | Poor | 0 |

TABLE 5 scores for combinations of CD20 (im) and CD3 (im):

| Name | Combination | Prognosis | Score |
|---|---|---|---|
| HiHi | Hi CD20 (im)/Hi CD3 (im) | Good | 2 |
| Het | [Hi CD20 (im)/Lo CD3 (im)] or [Lo CD20 (im)/Hi CD3 (im)] | intermediate | 1 |
| LoLo | Lo CD20 (im)/Lo CD3 (im) | Poor | 0 |

TABLE 6 scores for combinations of CD20 (im) and CD45RO (ct):

| Name | Combination | Prognosis | Score |
|---|---|---|---|
| HiHi | Hi CD20 (im)/Hi CD45RO (ct) | Good | 2 |
| Het | [Hi CD20 (im)/Lo CD45RO (ct)] or [Lo CD20 (im)/Hi CD45RO (ct)] | intermediate | 1 |
| LoLo | Lo CD20 (im)/Lo CD45RO (ct) | Poor | 0 |

TABLE 7 scores for combinations of CD20 (im) and CD45RO (im):

| Name | Combination | Prognosis | Score |
|---|---|---|---|
| HiHi | Hi CD20 (im)/Hi CD45RO (im) | Good | 2 |
| Het | [Hi CD20 (im)/Lo CD45RO (im)] or [Lo CD20 (im)/Hi CD45RO (im)] | intermediate | 1 |
| LoLo | Lo CD20 (im)/Lo CD45RO (im) | Poor | 0 |

TABLE 8 scores for combinations of CD20 (im), CD8 (ct) and CD8 (im):

| Name | Combination | Prognosis | Score |
|---|---|---|---|
| HiHiHi | Hi CD20 (im)/Hi CD8 (ct)/Hi CD8 (im) | Good | 3 |
| Het | [Hi CD20 (im)/Hi CD8 (ct)/Lo CD8 (im)] or [Hi CD20 (im)/Lo CD8 (ct)/Hi CD8 (im)] or [Lo CD20 (im)/Hi CD8 (ct)/Hi CD8 (im)] | intermediate | 2 |
| Het | [Hi CD20 (im)/Lo CD8 (ct)/Lo CD8 (im)] or [Lo CD20 (im)/Hi CD8 (ct)/Lo CD8 (im)] or [Lo CD20 (im)/Lo CD8 (ct)/Hi CD8 (im)] | intermediate | 1 |
| LoLoLo | Lo CD20 (im)/Lo CD8 (ct)/Lo CD8 (im) | Poor | 0 |

TABLE 9 scores for combinations of CD20 (im), CD3 (ct) and CD3 (im):

| Name | Combination | Prognosis | Score |
|---|---|---|---|
| HiHiHi | Hi CD20 (im)/Hi CD3 (ct)/Hi CD3 (im) | Good | 3 |
| Het | [Hi CD20 (im)/Hi CD3 (ct)/Lo CD3 (im)] or [Hi CD20 (im)/Lo CD3 (ct)/Hi CD3 (im)] or [Lo CD20 (im)/Hi CD3 (ct)/Hi CD3 (im)] | intermediate | 2 |
| Het | [Hi CD20 (im)/Lo CD3 (ct)/Lo CD3 (im)] or [Lo CD20 (im)/Hi CD3 (ct)/Lo CD3 (im)] or [Lo CD20 (im)/Lo CD3 (ct)/Hi CD3 (im)] | intermediate | 1 |
| LoLoLo | Lo CD20 (im)/Lo CD3 (ct)/Lo CD3 (im) | Poor | 0 |

TABLE 10 scores for combinations of CD20 (im), CD45RO (ct) and CD45RO (im):

| Name | Combination | Prognosis | Score |
|---|---|---|---|
| HiHiHi | Hi CD20 (im)/Hi CD45RO (ct)/Hi CD45RO (im) | Good | 3 |
| Het | [Hi CD20 (im)/Hi CD45RO (ct)/Lo CD45RO (im)] or [Hi CD20 (im)/Lo CD45RO (ct)/Hi CD45RO (im)] or [Lo CD20 (im)/Hi CD45RO (ct)/Hi CD45RO (im)] | intermediate | 2 |
| Het | [Hi CD20 (im)/Lo CD45RO (ct)/Lo CD45RO (im)] or [Lo CD20 (im)/Hi CD45RO (ct)/Lo CD45RO (im)] or [Lo CD20 (im)/Lo CD45RO (ct)/Hi CD45RO (im)] | intermediate | 1 |
| LoLoLo | Lo CD20 (im)/Lo CD45RO (ct)/Lo CD45RO (im) | Poor | 0 |

TABLE 11

Univariate analysis of Disease-free survival (DFS) among patients with UICC-TNM Stage I/II/III/IV colorectal cancer (cohort 107) according to clinical parameters or immune parameters

| | Disease-free survival (DFS) | | | |
|---|---|---|---|---|
| | Predictive Accuracy (%) | | Hazard ratio | P |
| According to clinical parameters | c-index | Cτ | (95% CI) | value* |
| CD20-im (Lo = 0, Hi = 1) | 60.33 | 59.77 | 4.04 (2.17-7.56) 1.00 (reference) | <0.0001** s |

TABLE 11-continued

Univariate analysis of Disease-free survival (DFS) among patients with UICC-TNM Stage I/II/III/IV colorectal cancer (cohort 107) according to clinical parameters or immune parameters

| | Disease-free survival (DFS) | | | | |
|---|---|---|---|---|---|
| | Predictive Accuracy (%) | | Hazard ratio | P | |
| According to clinical parameters | c-index | Cτ | (95% CI) | value* | |
| CD20-im-CD8-ct.I 0 1-2 3-CD8-im (LoLoLo = 0, LoLoHi/LoHiLo/HiLoHi/HiHiLo = 1, HiHiHi = 2) | 64.01 | 63.29 | 12.49 (2.46-63.46)*** 2.83 (1.24-6.47)*** 1.00 (reference) | 0.0083** 0.2884** | s |
| CD20-im-CD45RO-ct.I 0 1-2 3-CD45RO-im (LoLoLo = 0, LoLoHi/LoHiLo/HiLoHi/HiHiLo = 1, HiHiHi = 2) | 64.62 | 65.78 | 11.29 (2.56-49.78)*** 3.18 (1.08-9.32)*** | 0.0047** 0.4915** | s |

All categorical covariates are transformed into numerical ones before they enter into the cox model. The transformation rule is indicated next to the parameter name.
Cτ: time-dependent c-index presentation.
*Log-rank P value.
**P value correction with Altman et al.
***Corrected by Hollaender et al. s: significant.
CI denotes confidence interval.

REFERENCES

Throughout this application, various references describe the state of the art to which this invention pertains. The disclosures of these references are hereby incorporated by reference into the present disclosure.

1. Finn, O. J. Cancer immunology. N Engl J Med 358, 2704-2715 (2008).
2. Galon, J., et al. Type, density, and location of immune cells within human colorectal tumors predict clinical outcome. Science 313, 1960-1964 (2006).
3. Galon, J., Fridman, W. H. & Pages, F. The adaptive immunologic microenvironment in colorectal cancer: a novel perspective. Cancer Res 67, 1883-1886 (2007).
4. Pages, F., et al. Effector memory T cells, early metastasis, and survival in colorectal cancer. N Engl J Med 353, 2654-2666 (2005).
5. Jemal, A., et al. Cancer statistics, 2006. CA Cancer J Clin 56, 106-130 (2006).
6. Weitz, J., et al. Colorectal cancer. Lancet 365, 153-165 (2005).
7. Bindea, G., Mlecnik, B., Fridman, W. H., Pages, F. & Galon, J. Natural immunity to cancer in humans. Curr Opin Immunol 22, 215-222 (2010).
8. Pages, F., et al. In situ cytotoxic and memory T cells predict outcome in patients with early-stage colorectal cancer. J Clin Oncol 27, 5944-5951 (2009).
9. Atreya, I. & Neurath, M. F. Immune cells in colorectal cancer: prognostic relevance and therapeutic strategies. Expert Rev Anticancer Ther 8, 561-572 (2008).
10. Koebel, C. M., et al. Adaptive immunity maintains occult cancer in an equilibrium state. Nature 450, 903-907 (2007).
11. Shankaran, V., et al. IFN gamma and lymphocytes prevent primary tumour development and shape tumour immunogenicity. Nature 410, 1107-1111 (2001).
12. Smyth, M. J., Dunn, G. P. & Schreiber, R. D. Cancer immunosurveillance and immunoediting: the roles of immunity in suppressing tumor development and shaping tumor immunogenicity. Adv Immunol 90, 1-50 (2006).
13. June, C. H. Principles of adoptive T cell cancer therapy. J Clin Invest 117, 1204-1212 (2007).
14. June, C. H. Adoptive T cell therapy for cancer in the clinic. J Clin Invest 117, 1466-1476 (2007).

The invention claimed is:

1. A method for predicting the survival time of and treating a patient suffering from a solid cancer comprising the steps of:
   determining a density of CD20+ B cells at an invasive margin of a tumor (im) in a tumor tissue sample obtained from said patient;
   determining a density of one other cell type selected from CD8+ cytotoxic T cells or CD45RO+ memory T cells at the invasive margin of the tumor (im) and at a center of the tumor (ct), wherein the determining steps may be performed with the same or a different tumor tissue sample obtained from said patient;
   comparing each density determined in said determining steps with a predetermined reference value;
   providing:
   a) a good prognosis when:
   a1) the density of CD20+ B cells at the invasive margin of the tumor is higher than the predetermined reference value;
   a2) the density of said one other cell type at the invasive margin of the tumor (im) is higher than the predetermined reference value; and
   a3) the density of said one other cell type at the center of the tumor (ct) is higher than the predetermined reference value;
   b) an intermediate prognosis when:
   b1) the density of CD20+ B cells at the invasive margin of the tumor is higher than the predetermined reference value;
   b2) the density of said one other cell type at the invasive margin of the tumor (im) is lower than the predetermined reference value; and
   b3) the density of said one other cell type at the center of the tumor (ct) is higher than the predetermined reference value;
   or
   b'1) the density of CD20+ B cells at the invasive margin of the tumor is higher than the predetermined reference value;
   b'2) the density of said one other cell type at the invasive margin of the tumor (im) is higher than the predetermined reference value; and b'3) the density of said one other cell type at the center of the tumor (ct) is lower than the predetermined reference value;

or b''1) the density of CD20+ B cells at the invasive margin of the tumor is lower than the predetermined reference value b''2) the density of said one other cell type at the invasive margin of the tumor (im) is higher than the predetermined reference value; and b''3) the density of said one other cell type at the center of the tumor (ct) is higher than the predetermined reference value;

or bi) the density of CD20+ B cells at the invasive margin of the tumor is higher than the predetermined reference value bii) the density of said one other cell type at the invasive margin of the tumor (im) is lower than the predetermined reference value; and biii) the density of said one other cell type at the center of the tumor (ct) is lower than the predetermined reference value;

or b'i) the density of CD20+ B cells at the invasive margin of the tumor is lower than the predetermined reference value b'ii) the density of said one other cell type at the invasive margin of the tumor (im) is lower than the predetermined reference value; and b'iii) the density of said one other cell type at the center of the tumor (ct) is higher than the predetermined reference value;

or b''i) the density of CD20+ B cells at the invasive margin of the tumor is lower than the predetermined reference value b''ii) the density of said one other cell type at the invasive margin of the tumor (im) is higher than the predetermined reference value; and b''iii) the density of said one other cell type at the center of the tumor (ct) is lower than the predetermined reference value; or c) a poor prognosis when:

c1) the density of CD20+ B cells at the invasive margin of the tumor is lower than the predetermined reference value;

c2) the density of said one other cell type at the invasive margin of the tumor (im) is lower than the predetermined reference value; and c3) the density of said one other cell type at the center of the tumor (ct) is lower than the predetermined reference value;

and treating the patient with an appropriate anticancer treatment.

2. The method according to claim 1, wherein said one other cell type consists in CD8+ cytotoxic cells.

3. The method according to claim 1, wherein said one other cell type consists in CD45RO memory T cells.

4. The method according to claim 1, wherein said solid cancer is colorectal cancer.

5. A method for predicting the survival time of and treating a patient suffering from colorectal cancer comprising the steps of i) determining a density of CD20+ B cells at an invasive margin of a tumor (im) in a tumor tissue sample obtained from said patient, ii) comparing said density with a predetermined reference value, iii) providing a good prognosis when the density of B cells at the invasive margin of the tumor is higher than the predetermined reference value and a poor prognosis when the density of B cells at the invasive margin of the tumor is lower than the predetermined reference value; and iv) treating the patient with an anticancer treatment.

6. The method of claim 1, wherein the solid cancer is not melanoma.

7. A method for predicting the survival time of and treating a patient suffering from colorectal cancer comprising the steps of:

determining a density of CD20+ B cells at an invasive margin of a tumor (im) in a tumor tissue sample obtained from said patient;

determining a density of one other cell type selected from CD8+ cytotoxic T cells or CD45RO+ memory T cells at the invasive margin of the tumor (im) and at a center of the tumor (ct), wherein the determining steps may be performed with the same or a different tumor tissue sample obtained from said patient;

comparing each density determined in said determining steps with a predetermined reference value;

providing:

a) a good prognosis when:

a1) the density of CD20+ B cells at the invasive margin of the tumor is higher than the predetermined reference value;

a2) the density of said one other cell type at the invasive margin of the tumor (im) is higher than the predetermined reference value; and a3) the density of said one other cell type at the center of the tumor (ct) is higher than the predetermined reference value;

b) an intermediate prognosis when:

b1) the density of CD20+ B cells at the invasive margin of the tumor is higher than the predetermined reference value;

b2) the density of said one other cell type at the invasive margin of the tumor (im) is lower than the predetermined reference value; and b3) the density of said one other cell type at the center of the tumor (ct) is higher than the predetermined reference value;

or b'1) the density of CD20+ B cells at the invasive margin of the tumor is higher than the predetermined reference value;

b'2) the density of said one other cell type at the invasive margin of the tumor (im) is higher than the predetermined reference value; and b'3) the density of said one other cell type at the center of the tumor (ct) is lower than the predetermined reference value;

or b''1) the density of CD20+ B cells at the invasive margin of the tumor is lower than the predetermined reference value b''2) the density of said one other cell type at the invasive margin of the tumor (im) is higher than the predetermined reference value; and b''3) the density of said one other cell type at the center of the tumor (ct) is higher than the predetermined reference value;

or bi) the density of CD20+ B cells at the invasive margin of the tumor is higher than the predetermined reference value bii) the density of said one other cell type at the invasive margin of the tumor (im) is lower than the predetermined reference value; and biii) the density of said one other cell type at the center of the tumor (ct) is lower than the predetermined reference value;

or b'i) the density of CD20+ B cells at the invasive margin of the tumor is lower than the predetermined reference value b'ii) the density of said one other cell type at the invasive margin of the tumor (im) is lower than the predetermined reference value; and b'iii) the density of said one other cell type at the center of the tumor (ct) is higher than the predetermined reference value;

or b''i) the density of CD20+ B cells at the invasive margin of the tumor is lower than the predetermined reference value b''ii) the density of said one other cell type at the invasive margin of the tumor (im) is higher than the predetermined reference value; and b''iii) the density of said one other cell type at the center of the tumor (ct) is lower than the predetermined reference value; or c) a poor prognosis when:

c1) the density of CD20+ B cells at the invasive margin of the tumor is lower than the predetermined reference value;

c2) the density of said one other cell type at the invasive margin of the tumor (im) is lower than the predetermined reference value; and c3) the density of said one other cell type at the center of the tumor (ct) is lower than the predetermined reference value;

and treating the patient with an appropriate anticancer treatment.

* * * * *